United States Patent [19]

Naylor et al.

[11] 4,128,637
[45] Dec. 5, 1978

[54] PROCESS FOR PRODUCING THYMOSIN

[75] Inventors: Robert Naylor, Glendale; Howard F. Coyer, Wauwatosa, both of Wis.

[73] Assignee: Pabst Brewing Company, Milwaukee, Wis.

[21] Appl. No.: 809,083

[22] Filed: Jun. 23, 1977

Related U.S. Application Data

[63] Continuation of Ser. No. 669,862, Mar. 24, 1976, abandoned.

[51] Int. Cl.² .................. A61K 35/26; A61K 35/56; A61K 37/24
[52] U.S. Cl. .................................... 424/95; 424/177; 260/112.5 R; 260/112 R
[58] Field of Search .............................. 424/95, 177; 260/112.5 R

[56] References Cited

U.S. PATENT DOCUMENTS

| 3,657,417 | 4/1972 | Brunetti et al. | 424/95 |
| 4,010,148 | 3/1977 | Goldstein | 424/177 |

FOREIGN PATENT DOCUMENTS 1543203  9/1968  France .................................... 424/177

Primary Examiner—Donald B. Moyer
Attorney, Agent, or Firm—Richard L. Johnston

[57] ABSTRACT

Thymosin is produced by an improved process in which thymus glands are coarse ground, extracted in saline solution which is filtered and the filtrate or extract is injected with steam for a brief period of time to denature undesired proteins without denaturing the thymosin, whereby a precipitate is formed which is separated by filtration. The filtrate is concentrated and cooled and crude thymosin is precipitated by adding the concentrate to acetone.

2 Claims, No Drawings

PROCESS FOR PRODUCING THYMOSIN

RELATED APPLICATION

This application is a continuation of U.S. Ser. No. 669,862 filed Mar. 24, 1976 now abandoned.

BACKGROUND

The purification and properties of bovine thymosin have been described by Hooper et al, Annals New York Academy of Sciences, Vol. 249 p. 125-144 (1975). A process of preparing thymosin has also been described in British Pat. No. 1,195,980.

A crude thymosin which is referred to as "thymosin-fraction 3" is described by Hooper et al.

Thymosin-fraction 3 is a prime intermediate in the preparation of pure thymosin from calf thymus glands. Thymosin-fraction 3 contains all the thymosin originally present in the calf thymus glands but contains only 1% of the original weight of the glands. The greatly reduced bulk and the 100-fold purification allows the application of known and usual protein-purification procedures for the preparation of pure thymosin.

Purified thymosin is known to consist of several proteins with molecular weights ranging from 1,200-14,000. It has been shown to stimulate lymphoid tissue proliferation and to thereby increase immunity to infectious processes. Recent clinical trials involving immunodeficiency diseases have shown that thymosin increases the number of peripheral blood T-cells thereby partially restoring immunological competence.

Previous methods of extracting thymosin from thymus glands involved homogenizing the glands in saline solution and centrifuging the homogenate. Such processes are laborious for the extraction of large quantities (500-1,000 pounds) of thymus glands and result in the extraction of undesirable fatty constituents of the glands which interfere with subsequent processing. In the published procedures the heat-labile proteins in the saline extract are precipitated by heating the extract to 80° C. in a water bath. In previous procedures, the extract obtained after removing the heat-labile proteins is mixed directly with five or ten volumes of cold acetone to precipitate thymosin-fraction 3.

OBJECTS

One of the objects of the present invention is to provide a new and improved process for preparing thymosin in which thymosin-fraction 3 is prepared in a more simple manner than in previous processes and with a minimal production of interfering substances such as fats and undesired or inactive proteins.

Another object of the invention is to provide a process of the type described which is more economical than previous procedures. Other objects will appear hereinafter.

BRIEF SUMMARY OF THE INVENTION

Thymosin is produced by an improved process in which thymus glands are coarse ground, extracted in saline solution which is filtered and the filtrate or extract is injected with steam for a brief period of time to denature undesired proteins without denaturing the thymosin, whereby a precipitate is formed which is separated by filtration. The filtrate is concentrated and cooled and crude thymosin is precipitated by adding the concentrate to acetone.

DETAILED DESCRIPTION OF THE INVENTION

In the practice of the invention frozen thymus glands such as, for example, calf thymus glands, are ground in a meat grinder so as to produce relatively coarse ground particles having diameters of about 1/16 inch to 3/16 inch. These coarse particles are then extracted by stirring with a saline solution in a conventional manner. The solids are filtered preferably by using a filter aid such as diatomaceous earth or any other suitable filter aid, and the filter cake is discarded. The filtrate in the form of a flowing stream is then brought into contact with steam by injecting steam under superatmospheric pressure into the flowing stream so as to bring the filtrate instantaneously to a temperature of around 80°-85° C. The time during which the filtrate is held at this temperature should be at least sufficient to denature the undesired protein but not long enough to denature thymosin. Usually instantaneous heating for a period of at least one minute is required.

Either low pressure steam, for example, at 15 psig, or high pressure steam, for example, at 60 psig, can be used to provide instantaneous heating. Usually not more than several minutes are required. This produces a suspension of precipitated protein which is then cooled, preferably by discharging it on ice, and filtered, preferably with the assistance of a filter aid such as, for example, diatomaceous earth. The filtration is preferably accomplished by using a filter press and the filter cake is discarded.

The resultant filtrate is preferably concentrated to about one-half its volume and cooled to a relatively low temperature, usually around 4° C. The concentrate is then added to a larger volume of acetone which has been cooled to a lower temperature than the concentrate, preferably to a temperature around −10° C. This gives a precipitate of crude thymosin. The supernatant liquid can be decanted and the thymosin collected by filtration, washed with fresh acetone and dried under vacuum drying conditions.

The invention will be further illustrated but is not limited by the following example in which the quantities are given in parts by weight unless otherwise indicated.

EXAMPLE 500 pounds of frozen calf thymus glands were ground in a meat grinder and the ground glands were mixed with 185 gallons of 0.15M sodium chloride at 4° C. for 5-30 minutes.

250 pounds of filter aid were stirred into the mixture and the mixture was filtered on a filter press. The filter cake was discarded. The filtrate was brought to 80°-85° C. by injecting steam into a flowing stream of the extract and allowing the steam and extract to remain in contact with each other for 1-2 minutes. The resultant suspension of precipitated protein was discharged onto 200 pounds of ice, 80 pounds of filter aid were added and the resulting slurry was filtered on a filter press. The filter cake was discarded.

The 200 gallons of filtrate were concentrated to 100 gallons and cooled to 4° C. The concentrate was added to 400 gallons of acetone cooled to −10° C. This gave a precipitate of crude thymosin. The supernatant was decanted and the thymosin was collected by filtration, washed with fresh acetone and dried in vacuo. The dried powder weighed 2,500 g.

As contrasted with previous processes in which thymus glands have been homogenized in saline solution and centrifuged, the present process is much simpler in that the frozen thymus glands are ground with a meat grinder and the ground glands are extracted by stirring with saline solution. By this method 500 pounds of calf thymus glands can be ground and extracted in one hour. Furthermore, by coarse grinding rather than homogenizing, the release of interfering substances, especially fat, is kept at a minimum, and the extract is substantially free of fatty material and can be readily filtered on a filter press.

Thymosin is soluble in dilute saline solution such as, for example, 0.15 molar sodium chloride in water. Any dilute aqueous saline solution capable of extracting the thymosin can be used in the initial extraction.

Whereas in the published procedures the heat-labile proteins in the saline extract are precipitated by heating the extract to 80° C. in a water bath, in the present invention the heat-labile proteins are precipitated by injecting steam into a flowing stream of the extract, thereby raising the temperature of the stream to 80° C. instantaneously and holding the temperature of the extract at 80° C. for 1-2 minutes. The stream is then pumped onto ice to reduce the temperature, mixed with filter aid and filtered on a filter press. This process provides for the precipitation of the unwanted heat-labile proteins but the rapid heating (as contrasted to heating on a water bath) minimizes the time period during which the extract is held at a high temperature, thus lowering the risk of denaturing the thymosin and preserving the integrity of the thymosin.

While in previous procedures the extract obtained after removing the heat-labile proteins is mixed directly with 5 or 10 volumes of cold acetone to precipitate thymosin-fraction 3, in the present invention it is concentrated in vacuo at 25°-30° C., preferably to one half of its original volume. The final concentrated extract is then added to four to ten times its volume of cold acetone to precipitate thymosin-fraction 3. This process yields the same quantity of fraction 3 as the published procedures but reduces the quantity of acetone required by 50% and greatly simplifies the precipitation and collection procedures.

It is believed to be apparent, therefore, that the present invention greatly facilitates the preparation of thymosin. While crude thymosin (thymosin-fraction 3) usually contains less than 1% by weight thymosin, it will be understood that this can be further purified in any suitable manner, for example, by the procedures described in the previously mentioned references.

It will also be understood that the invention is susceptible to some variation and modification in its practical application. Thus, while instantaneous heating of the saline solution extract is preferably accomplished by injection of steam into a stream of said solution, the heating might also be accomplished by high intensity rays or by means of conventional heat exchangers or in any other manner which does not inactivate or denature the thymosin.

The concentration of the filtrate prior to addition to acetone is preferably accomplished by evaporation in vacuo usually at a temperature around 30° C.

The invention is hereby claimed as follows:

1. In a process for producing thymosin-fraction 3 wherein calf thymus glands are extracted in aqueous saline solution, undissolved material is removed, the resultant liquid material is heated, after heating the resultant product is cooled, the precipitate formed on cooling is removed, acetone is added to the resultant liquid in sufficient amount to precipitate thymosin-fraction 3 and the resultant precipitate is recovered, the improvement which comprises in combination:
   (a) grinding calf thymus glands to a coarse state with a meat grinder,
   (b) mixing the ground glands with an 0.15M sodium chloride solution, thereby forming a suspension,
   (c) filtering the resultant suspension on a filter press with the aid of a filter aid,
   (d) heating the resultant filtrate instantaneously to 80°-85° C. by injecting steam under superatmospheric pressure into a flowing stream of the filtrate,
   (e) maintaining the said temperature of 80°-85° C. for a period of approximately 1-2 minutes, said period being at least sufficient to denature the undesired protein but not long enough to denature thymosin,
   (f) rapidly cooling the resultant product,
   (g) filtering off the resultant precipitate,
   (h) concentrating the filtrate to approximately half its volume,
   (i) adding acetone to the concentrated filtrate in sufficient amount to precipitate thymosin-fraction 3, and
   (j) recovering the resultant precipitate.

2. A process as claimed in claim 1 in which the resultant product in step (f) is rapidly cooled by discharging it onto ice.

* * * * *